| United States Patent [19] | [11] | 4,144,266 |
|---|---|---|
| Plummer et al. | [45] | Mar. 13, 1979 |

[54] SULFONATION OF CRUDE OILS TO PRODUCE PETROLEUM SULFONATES

[75] Inventors: Mark A. Plummer; Donald E. Schroeder, Jr., both of Littleton, Colo.

[73] Assignee: Marathon Oil Company, Findlay, Ohio

[21] Appl. No.: 376,657

[22] Filed: Jul. 5, 1973

[51] Int. Cl.$^2$ .......................................... C07C 143/24
[52] U.S. Cl. .................................................. 260/505 S
[58] Field of Search ................. 260/505 S; 252/8.5 P, 252/8.55 D

[56] References Cited

U.S. PATENT DOCUMENTS

| Re. 22,548 | 9/1944 | Brandt | 260/505 S |
|---|---|---|---|
| 1,822,271 | 9/1931 | Coggeshall | 252/8.55 D |
| 2,798,851 | 7/1957 | Nelson et al. | 252/8.5 P |
| 2,953,525 | 9/1960 | Young | 252/8.5 P |
| 3,215,628 | 11/1965 | Peacock | 260/505 S |
| 3,270,038 | 8/1966 | Marshall et al. | 250/505 S |
| 3,653,437 | 4/1972 | Gale | 166/252 |

*Primary Examiner*—A. Siegel
*Attorney, Agent, or Firm*—Joseph C. Herring; Jack L. Hummel

[57] ABSTRACT

Petroleum sulfonates are obtained by treating whole crude oil or topped crude oil or mixtures thereof with sulfur trioxide, removing unreacted hydrocarbon, e.g., by addition of water, and neutralizing the sulfonic acids formed with a base, e.g., sodium hydroxide or ammonia. The products have particular utility for the preparation of micellar systems for use in secondary-type petroleum recovery.

25 Claims, 1 Drawing Figure

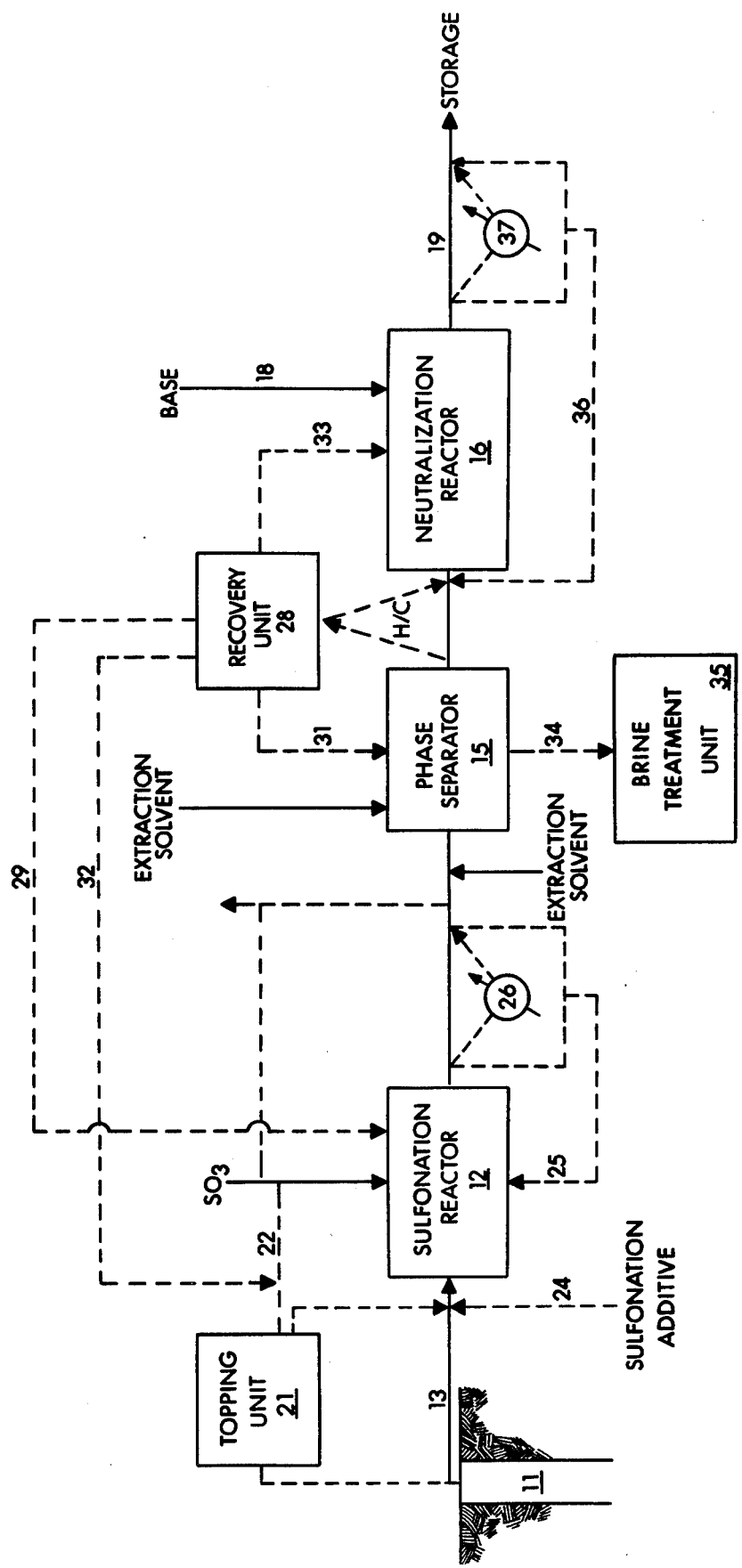

SULFONATION OF CRUDE OILS TO PRODUCE PETROLEUM SULFONATES

BACKGROUND OF THE INVENTION

This invention relates to compositions for oil treating generally classified in U.S. Patent Office Class 252, subclass 8.55, and to Chemistry of the Carbon Compounds, sulfonation products of aromatic mixtures classified in Class 260, subclass 505.

Petroleum sulfonates have been prepared by a variety of means, for example, sulfonated with sulfur dioxide (U.S. Pat. No. 2,999,812), sulfur dioxide and chlorine (U.S. Pat. No. 2,197,800), oleum (U.S. Pat. No. 2,845,455), and sulfur trioxide (U.S. Pat. No. 3,183,183). U.S. Pat. Nos. 3,215,628 and 2,815,370 teach the use of specific hydrocarbon fractions. Other patents of lesser interest include U.S. Pat. Nos. 2,174,508; 2,800,962; 3,173,864; 3,308,068; 3,244,622; and 3,418,239.

The prior art suggests that whole crude oil can be sulfonated and used in oil production. (See U.S. Pat. Nos. 1,822,271; 3,126,952; and 3,302,713 teaching the use of whole crude sulfonates in secondary-type oil recovery and U.S. Pat. Nos. 2,798,851; 2,953,525; and 3,198,832 teaching use of such sulfonates in drilling muds.) However, we are unaware of a teaching as to how this can be done or any commercial use of such a process. Specific teachings of which we are aware require the removal of the light and/or heavy ends and the use of only the middle cuts to manufacture the petroleum sulfonates.

There are a number of reasons for fractionating crudes prior to sulfonation. Inter alia, it is difficult to obtain a marketable product from asphaltenes which tend to form tarry materials which foul reactors and sometimes form coke-like deposits. Also, the light ends are often aliphatics or light aromatics which will not produce the desired product.

We have now discovered that commercially acceptable sulfonates can be prepared from a variety of crude oils using our processes. While we were surprised to be able to prepare sulfonates in good yields and without coking or the formation of tarry products, we were pleased when we found that the sulfonates produced form economic micellar systems suitable for use in oil recovery.

The upcoming "energy crisis" puts our invention in context. T. M. Geffen (*Oil & Gas Journal,* May 7, 1973, pp. 66–76) indicates that 55 billion barrels of additional crude can be recovered via tertiary recovery. Heretofore, tertiary recovery processes (see U.S. Pat. Nos. 3,254,714; 3,307,628; 3,504,744; 3,261,399; 3,497,006; 3,506,070; 3,354,953; 3,330,344 and 3,348,611—most using petroleum sulfonate surfactants) have all proved uneconomic because, inter alia, the cost of materials used made the processes uneconomic and the amounts of oil recovered were too small. Our process provides sulfonates at a price sufficiently low to aid substantially in the commercialization of tertiary oil recovery using secondary-type oil recovery techniques taught in the above listed patents.

This "tertiary" oil is a resource which will not create balance of payments problems and which cannot be withheld by foreign governments and our process should be considered within this context.

SUMMARY OF INVENTION

In the present invention, whole crude oil is reacted with $SO_3$, unreacted hydrocarbons are removed, and the sulfonic acids are neutralized. The use of our process increases plant throughput per unit of capital cost as the phase separation time of the unreacted hydrocarbon from the sulfonic acids is significantly reduced and the amounts of unreacted hydrocarbon recovered are appreciably increased. Using our processes, portable sulfonation facilities can be set up in the oil field. The advantages of the processes are obvious when compared with existing techniques requiring transportation of crude to an off-site location, refining the crude to produce a selected fraction for sulfonation, sulfonation of the refined hydrocarbon, neutralization and transportation of the neutralized product to the oil field for use. While the sulfonates produced by the present invention are intended to find their primary use in oil recovery, they, or fractions thereof, are also useful for the usual applications, such as flotation, cutting oils, insecticide carriers, to which petroleum sulfonates are put.

GENERAL DESCRIPTION OF INVENTION

FIG. 1 schematically depicts our process and a number of optional procedures which can be used therewith. Basically, crude oil from well 11 and $SO_3$ vapor enter sulfonation reactor 12 through lines 13 and 14 respectively. Desired amounts of any solvent, unreacted hydrocarbons and sulfonic acids are removed in phase separator 15. The sulfonic acids and a base are introduced into neutralization reactor 16 through lines 17 and 18 to form the desired sulfonation product which passes through line 19 to storage.

A number of optional steps (indicated by dashed lines) enhance the variety and characteristics of sulfonates which can be obtained, the purity of these products and the economics of the process. Thus, low molecular weight hydrocarbons can be removed in topping unit 21 and mixed, via line 22, with the $SO_3$ for dilution purposes. The higher molecular weight hydrocarbon feedstocks are charged to reactor 12 through line 23. Sulfonation additives can be introduced through line 24. Desired amounts of reaction products (sulfonic acids, $SO_2$, sulfuric acid, unreacted hydrocarbons and reaction solvent, if any) can be recycled to reactor 12 through line 25 either before or after passage through cooler 26. Gaseous or vaporous products can be removed and, preferably, recycled as an $SO_3$ diluent through line 27. One or more recovery units 28 can be used to separate sulfonic acids, reaction solvent, extraction solvent, diluents, unreacted hydrocarbons, etc. Reaction solvent can be recycled to the process through line 29 to reactor 12 and extraction solvent to phase separator 15 through line 31, diluent through line 32, and sulfonic acids passed to neutralization reactor 16 through line 33. Brine passing through conduit 32 can be cleaned up in brine treatment unit 35. If necessary, a portion of the neutralized product can be recycled to neutralization reaction 16 through line 36, either before or after passage through cooler 37.

Those sulfonation reactors conventionally utilized for the hydrocarbon sulfonation including, for example, the falling film, scraped surface and stirred tank reactors may be used in our process. In those instances where an $SO_3$ diluent is used, we prefer to use a back mixed tubular reactor. All materials should be in turbulent flow on entering the preferred tubular reactor.

The term "crude oil" as used herein includes whole crudes, crude oils which have been "topped" to remove the lighter ends having boiler points below about 300° F. and more preferably below about 600° F. and mixtures of whole and topped crudes. The crude oils may be pure hydrocarbons or may contain sulfur, halogen, and nitrogen moities.

Preferred crude oils are those with aromatic or olefinic portions having molecular weights in the range from about 200 to about 1000, more preferably from about 300 to about 800, and most preferably from about 350 to about 500. The percent aromatics and olefins in the crude oil is preferably from about 10 to about 95, more preferably from about 20 to about 80, and most preferably from about 25 to about 50 weight percent.

Additional materials can be introduced into the sulfonation reactor. These include known catalysts, which do not appear to be needed but may be used if desired, "sulfonation additives" which, inter alia, may aid in controlling the equivalent weight distribution of the product mixture, and reaction solvents which are used to dilute the $SO_3$, promote a more even sulfonation reaction, insure solution of the sulfonic acids in any unreacted hydrocarbons, and lower the viscosity of the reaction products. The additives are useful in amounts ranging from about 0 to about 20, more preferably from about 1 to about 15, and most preferably from about 2 to about 10 lbs additive per 100 lbs crude oil feedstock. The additives are often sulfonated or sulfated and become a component of the product mixture and can be incorporated in the feedstocks before or during sulfonation.

Useful additives include aromatic hydrocarbons, olefinic hydrocarbons or oxygenated hydrocarbons and preferably have molecular weights in the range from about 200 to about 1000, more preferably from about 300 to about 800, and most preferably from about 350 to about 500.

Specific examples of additives include oxo alcohol bottoms (see "Higher Oxo Alcohols" by L. F. Hatch, Enjay Company, Inc., 1957, and Industrial & Engineering Chemistry, Vol. 51, No. 3, pp. 257-258); oxo alcohols alkylated with 1-50 moles of alkylene oxides, such as ethylene or propylene oxide; catalytic cycle oil aromatics (see U.S. Pat. No. 3,317,442); Ultraformer polymer bottoms (mixtures of alkylated benzene and asphaltenes).

A commercial $SO_3$ feed is preferred which is free of impurities, such as $H_2SO_4$, which can cause deleterious side reactions, and is anhydrous. From about 5 to about 30, more preferably from about 7 to about 20, and most preferably from about 8 to about 15 lbs $SO_3$ can be fed to the sulfonation reactor per 100 lbs crude oil.

The $SO_3$ can be diluted with liquid or gaseous low molecular weight aliphatics, $SO_2$, air, nitrogen or other inert gases with a ratio of diluent to $SO_3$ of about 0 to about 10, more preferably from about 1 to about 6, and most preferably from about 2 to about 4 moles/mole.

A reaction solvent, such as ethylene dichloride, trichloroethylene, nitrobenzene, nitropropane and like substantially inert polar solvents can be introduced into the reactor to dissolve the sulfonic acids in the unreacted hydrocarbons. Heavy viscous crudes often require a solvent while less viscous crudes can be sulfonated with or without such a solvent. Where necessary, solvent concentrations are typically from about 0 to about 20 lbs, preferably from about 1 to about 10 lbs, and more preferably from about 3 to about 8 lbs solvent per lb $SO_3$.

The preferred $SO_3$ diluent is a recycle of the light ends from reaction 12 obtained by a 1-stage flash and containing a mixture of $SO_2$ and light hydrocarbons.

Reaction conditions are not narrowly critical. The temperatures will normally be in the range of from about 80° to about 250°, more preferably from about 100° to about 200°, and most preferably from about 130° to about 180° F. Pressures will range from about 0.01 to about 150, more preferably from about 0.15 to about 75, and most preferably from about 0.2 to about 5 atmospheres. Reaction times will be from 0.001 to 3600, more preferably 0.01 to 360, and most preferably 0.02 to 60 seconds.

The reaction products are fractionated as desired. Preferably, any reaction solvent will then first be removed, e.g., by steam stripping, and the remaining products treated with an extraction solvent to free the sulfonic acids from any unreacted hydrocarbon. Examples of the extraction solvent include water, the low molecular weight aliphatic or halogenated alcohols, ketones, ethers and the more polar hydrocarbons, such as benzene and toluene.

Preferably, the amount of salts and unreacted hydrocarbon in the final product are controlled by regulating the extraction solvent to reaction products ratio and the make up of the extraction solvent. Thus, from about 0.8 to about 2.0 lbs, preferably 1.0 to about 1.8 lbs, and more preferably 1.1 to about 1.5 lbs of aqueous alcohol solution or water is mixed with each lb of reaction products. The aqueous alcohol is preferably isopropyl alcohol (IPA)/water solution. The extraction solvent composition by weight is preferably about 50 to about 80% IPA, and more preferably about 55 to 75% IPA by weight.

Either 2 or 3 phases will result from the addition of the extraction solvent. From top to bottom, these include a raffinate phase consisting primarily of unreacted hydrocarbons, an extract phase containing most of the sulfonic acids and, depending upon whether alcohol is used, a brine phase containing sulfurous and sulfuric acids.

The extraction solvent, if any, is separated from the raffinate and extract phases, e.g., by stripping. If water is the extraction solvent, it will preferably remain with the sulfonic acids. The brine phase can be neutralized and the salts removed therefrom for further processing to recover acids. The extract phase is then neutralized in reactor 16 with sufficient base, preferably a monovalent base, such as sodium or potassium hydroxide or ammonia, etc., to form a neutralized petroleum sulfonate.

The neutralized sulfonate should have an average equivalent weight, the sulfonate molecular weight divided by the average number of sulfonate groups per molecules, within the range of about 350 to about 525, more preferably about 375 to about 475 and most preferably about 390 to about 445 if micellar systems for use in secondary-type oil recovery. Micellar dispersions used in secondary-type oil recovery are taught in the previously listed U.S. patents. If water-soluble petroleum sulfonates are the desired products, the equivalent weights will be lower and directly related to the desired degree of hydrophilicity.

The following examples more specifically teach the process of our invention.

EXAMPLE I

Crawford County crude oil was contacted with 10.1 lbs $SO_3$ per 100 lb crude diluted in 3.0 moles of a recycled mixture of $SO_2$ and light hydrocarbon per mole of $SO_3$ in a back-mix tubular reactor. The reactor was maintained at about 158° F. and 13 psia. 1.26 lbs water was added per lb reaction products to remove 0.62 lb unreacted hydrocarbon/1.00 lb reaction products. The extract phase was neutralized with 0.10 lb 28% $NH_4OH$ to a pH of 7. The unreacted hydrocarbon-sulfonic acid settling time was 66 min/ft total liquid height.

EXAMPLE II

The reactor of Example I was used and the procedures of Example I were changed only by removing the unreacted hydrocarbons after neutralization (0.029 lb $NH_3$ + 1.26 lb water). 0.48 lb unreacted hydrocarbon/1.0 lb reaction products was removed. Settling time was 118 min/ft total liquid height.

EXAMPLE III

Table A

| EXAMPLE | Micellar Dispersion Compositions (Wt %) in Examples | | | |
|---|---|---|---|---|
| | $-SO_3NH_4$ | $(NH_4)_2SO_4$ | n-hexanol | Water |
| I | 3.5 | 3.7 | 0.9 | 78.4 |
| II | 3.0 | 3.1 | 0.4 | 75.2 |

Balance is organic portion of sulfonate plus crude oil.

Using procedures broadly taught in the cited patents, micellar dispersions having the compositions of Table A were made by blending the sulfonates produced by the processes of Examples I and II with the other listed components with stirring. The compositions differ because of the necessity of matching the mobility of the micellar dispersion with that of the oil and water in the core. Three sets of paired cores were made by cutting into two equilength cores three 3" dia. × 4' Berea sandstone cores.

Table B

| Property Measured | EX. | Core Pairs | | |
|---|---|---|---|---|
| | | First | Second | Third |
| Permeability | I | 302 | 174 | 276 |
| | II | 317 | 182 | 267 |
| Oil Saturation % Pore Vol. | I | 32.3 | 32.7 | 30.3 |
| | II | 32.3 | 32.6 | 35.5 |

The core pairs had the permeability and oil saturation of Table B. The cores were then saturated with water, flooded with Illinois Basin crude oil obtained from the North Crawford County Pipe Line until no additional water was displaced and then waterflooded with a simulated conate water until no additional oil was produced. 6% pore volume (pv) of the micellar dispersion formed from the sulfonate of Example I was injected into one set of the paired cores and 7% pv of the micellar dispersion formed from the sulfonate of Example II was injected into the remaining paired cores to balance sulfonate content. The micellar systems were displaced through the cores with a series of aqueous solutions made up of ICI 222-A partially hydrolyzed polyacrylamide polymer dissolved in Palestine water. The first injected aqueous solution was 10% of pv and contained a 1000 ppm of polymer; the second 54% pv contained 404 ppm polymer; and the third 30% pv contained 50 ppm polymer; and the fourth, 50% pv simulated Henry Plant water. The "tertiary" oil recovered is the percent of residual oil left after waterflooding which was recovered by the above described procedures. The following table sets out the oil recoveries obtained from the paired cores:

Table C

| EXAMPLE | Oil Recovery % of Oil in Place in Core Pairs | | |
|---|---|---|---|
| | First | Second | Third |
| I | 74.9 | 71.6 | 93.8 |
| II | 72.2 | 63.7 | 74.9 |

The tendency of the data of Example III, considering the potential error inherent in such flooding, indicates that the sulfonates prepared by our processes may have improved characteristics for oil recovery processes.

Modifications of our invention obvious to those skilled in the art are intended to be within the scope of specification and the following claims.

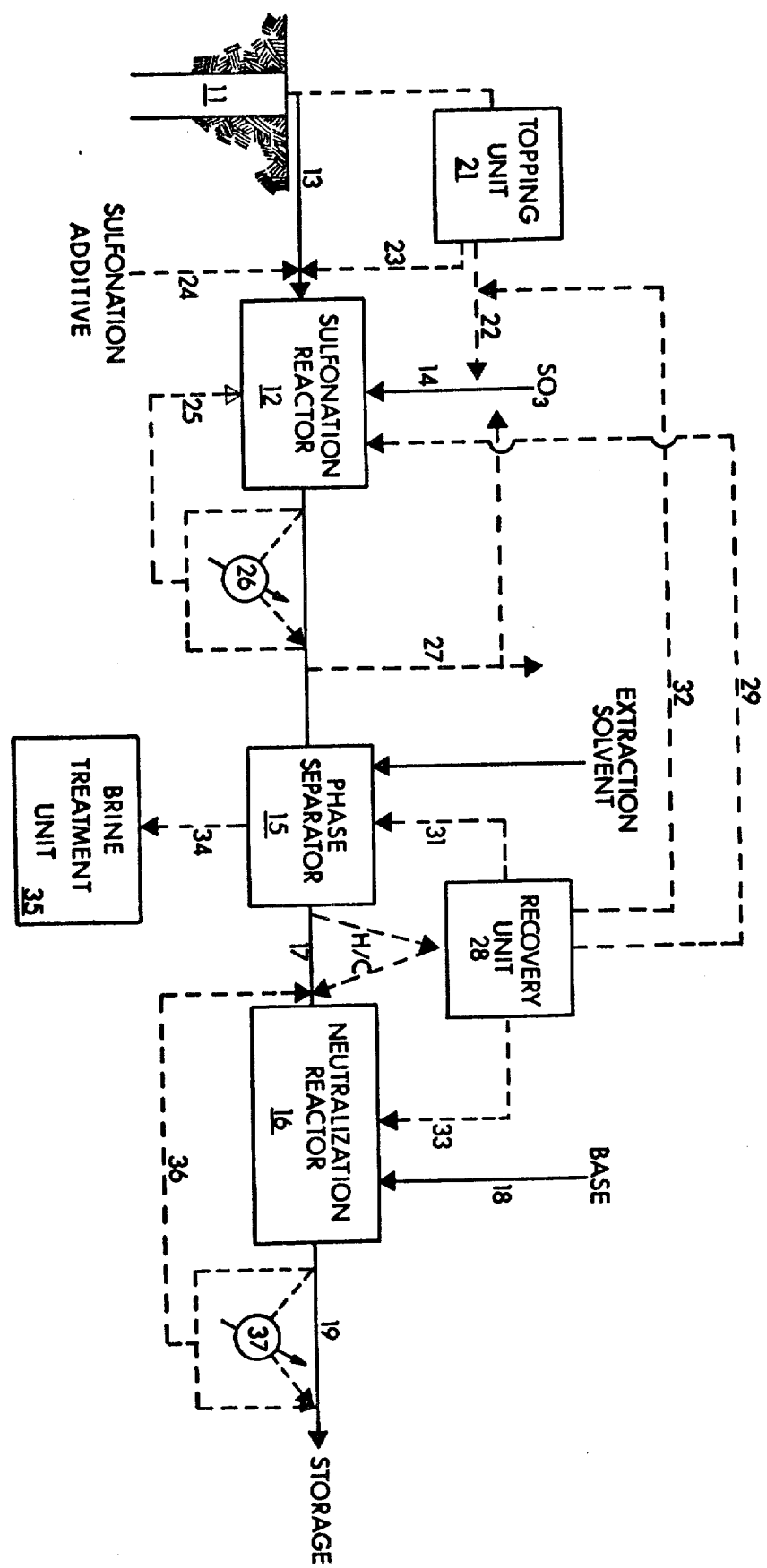

What is claimed is:

1. In a process for the preparation of petroleum sulfonates comprising contacting sulfur trioxide with a hydrocarbon selected from the group consisting of whole crude oil, topped crude oil, and mixtures thereof in a reaction zone, at a temperature of from about 80° to about 250° F., at a pressure of from about 0.01 to about 150 atmospheres, and for a reaction time of from about 0.001 to about 3600 seconds wherein from about 5 to about 30 lbs. of sulfur trioxide are contacted with each 100 lbs. of hydrocarbon, the improvement comprising removing unreacted hydrocarbons after said contact with sulfur trioxide and thereafter neutralizing, with base, the produce obtained by said contact with sulfur trioxide, wherein said removal of hydrocarbons comprises the step of extracting the product mixture resulting from said contact of said sulfur trioxide with said hydrocarbon by contacting said product mixture with from about 0.8 to about 2.0 lbs. of an extraction solvent per lb. of said product mixture.

2. A process according to claim 1 wherein said contact with said sulfur trioxide occurs in the presence of from about 0 to about 20 lbs of a reaction solvent, substantially inert to reaction with said sulfur trioxide, per lb of said $SO_3$ present in said reaction zone.

3. A process according to claim 1 wherein said contact with said sulfur trioxide occurs in the presence of from about 0 to about 10 moles of an $SO_3$ diluent, substantially inert to reaction with said sulfur trioxide, per mole of said $SO_3$ present in said reaction zone.

4. A process according to claim 1 wherein said contact with said sulfur trioxide occurs in the presence of from about 0 to about 20 lbs. of a reaction solvent per lb. $SO_3$ and from about 0 to about 10 moles of an $SO_3$ diluent, per mole of $SO_3$, both substantially inert to reaction with said sulfur trixoide.

5. A process according to claim 1 wherein said contact with said sulfur trioxide occurs in the substantial absence of any reaction solvent or $SO_3$ diluent.

6. A process according to claim 2 wherein said solvent is selected from the group consisting of: ethylene dichloride, trichloroethane, nitrobenzene, nitropropane, and mixtures thereof.

7. A process according to claim 1 wherein said contact between said sulfur trioxide and said hydrocarbon occurs in a reaction zone and wherein a portion of the products from said reaction zone are recycled back to said reaction zone for contact with additional quantities of sulfur trioxide and said hydrocarbon.

8. A process according to claim 2 wherein said contact between said sulfur trioxide and said hydrocarbon occurs in a reaction zone and wherein a portion of the products from said reaction zone are recycled back to said reaction zone for contact with additional quantities of sulfur trioxide and hydrocarbon.

9. A process according to claim 7 wherein said contact with said sulfur trioxide occurs in the presence of from about 0 to about 10 moles of an $SO_3$ diluent, substantially inert to reaction with said sulfur trioxide, per mole of said $SO_3$ present in said reaction zone.

10. A process according to claim 8 wherein said contact with said sulfur trioxide occurs in the presence of from about 0 to about 20 lbs. of a reaction solvent per lb. of $SO_3$ and from about 0 to about 10 moles of an $SO_3$ diluent per mole of $SO_3$, both substantially inert to reaction with said sulfur trioxide.

11. A process according to claim 7 wherein said contact with said sulfur trioxide occurs in the substantial absence of any reaction solvent or $SO_3$ diluent.

12. A process according to claim 3 wherein the inert diluent is selected from the group of liquids or gases consisting of $SO_2$, refined light paraffins, crude oil light ends, air, nitrogen, natural gas, and mixtures thereof.

13. A process according to claim 8 wherein said contact between said sulfur trioxide and said hydrocarbon occurs in the substantial absence of any diluent.

14. A process according to claim 1 wherein said hydrocarbon has an average molecular weight in the range of about 200 to about 1,000, contains from about 10 to about 95% by weight aromatics.

15. A process according to claim 9 wherein the inert diluent is selected from the group consisting of liquid or gas-$SO_2$ refined light paraffins, crude oil light ends, air, nitrogen, natural gas, and mixtures thereof.

16. A process according to claim 2 wherein the contact between said $SO_3$ and said hydrocarbon occurs in the presence of from 0 to about 10 moles of an inert diluent per mole of $SO_3$.

17. A process according to claim 1 wherein said hydrocarbon consists essentially of whole crude oil.

18. A process according to claim 1 wherein said hydrocarbon consists essentially of topped crude oil.

19. A process according to claim 1 wherein said contact between said sulfur trioxide and said hydrocarbon occurs in the presence of an additive having a molecular weight in the range of from about 200 to about 1,000 and being selected from the group consisting of aromatic hydrocarbons, olefinic hydrocarbons, oxygenated hydrocarbons, and mixtures thereof.

20. In a process for the preparation of sulfonates useful in the preparation of micellar dispersions for supplemented recovery of oil, said sulfonates having average equivalent weight of from about 350 to about 525, by contacting sulfur trioxide with hydrocarbon comprising a whole crude oil, a topped crude oil, or mixture thereof, at a temperature of from about 80° to about 250° F., at a pressure of from about 0.01 to about 150 atmospheres, and for a reaction time of from about 0.001 to about 3600 seconds wherein from about 5 to about 30 lbs. of sulfur trioxide are contacted with each 100 lbs. of hydrocarbon, the improvement comprising removing unreacted hydrocarbons after said contacting with said sulfur trioxide and thereafter neutralizing with monovalent base, wherein said removal of hydrocarbons comprises the step of extracting the product mixture resulting from said contact of said sulfur trioxide with said hydrocarbon by contacting said product mixture with an extraction solvent.

21. A process according to claim 4 wherein said contact between said sulfur trioxide and said hydrocarbon occurs in the presence of a solvent selected from the group consisting of ethylene dichloride, trichloroethane, nitrobenzene, nitropropane, and mixtures thereof in the further presence of an $SO_3$ diluent selected from the group consisting of $SO_2$, refined light paraffins, crude oil light ends, air, nitrogen, hydrocarbon gases, and mixtures thereof at a temperature of from about 80° to about 250° F., and a pressure of from about 0.01 to about 150 atmospheres, and wherein there are present for each lb. of sulfur trioxide from about 1 to about 20 lbs. of said solvent and from about 1 to about 10 moles of said diluent per mole of said $SO_3$.

22. A process according to claim 21 wherein said contact between said sulfur trioxide and said hydrocarbon occurs in a reaction zone and wherein a portion of the products from said reaction zone are recycled back to said reaction zone for contact with additional quantities of sulfur trioxide and hydrocarbon.

23. A process according to claim 20 wherein said extraction solvent is selected from the group consisting of alcohols containing from 1 to about 5 carbon atoms, semi-polar organic compounds, water, and mixtures thereof.

24. A process according to claim 20 wherein said extraction solvent comprises aqueous isopropanol solution containing about 50 to about 80% by weight of isopropanol.

25. A process according to claim 20 wherein said product mixture upon contact with said extraction solvent forms three phases consisting of a raffinate phase comprising substantial quantities of unreacted hydrocarbon, an extract phase comprising substantial quantities of sulfonic acids, and a brine phase comprising $H_2SO_4$, $H_2SO_3$, and water.

* * * * *

UNITED STATES PATENT AND TRADEMARK OFFICE
CERTIFICATE OF CORRECTION

PATENT NO. : 4,144,266

DATED : March 13, 1979

INVENTOR(S) : Mark A. Plummer, Donald E. Schroeder, Jr.

It is certified that error appears in the above-identified patent and that said Letters Patent are hereby corrected as shown below:

Column 2, Line 57:   Delete "32" and insert -- 34

Column 6, line 34:   Delete "produce" and insert -- product

Canceled the sheet of drawing and substitute the attached sheet therefore.

Signed and Sealed this

Twentieth Day of November 1979

[SEAL]

Attest:

RUTH C. MASON
Attesting Officer

LUTRELLE F. PARKER
Acting Commissioner of Patents and Trademarks